United States Patent [19]

Keller

[11] 4,267,455
[45] May 12, 1981

[54] PURIFICATION APPARATUS

[75] Inventor: Hans U. Keller, Zürich, Switzerland

[73] Assignee: Katadyn Produkte AG, Switzerland

[21] Appl. No.: 96,601

[22] Filed: Nov. 21, 1979

[30] Foreign Application Priority Data

Nov. 24, 1978 [DE] Fed. Rep. of Germany ....... 2851013

[51] Int. Cl.³ ............................................... C02F 1/32
[52] U.S. Cl. .................................... 250/431; 250/436;
210/192; 210/198.1; 422/24
[58] Field of Search ............ 250/431, 432 R, 435–438;
210/64, 199, 192, 198 R; 422/24

[56] References Cited

U.S. PATENT DOCUMENTS

| 3,836,781 | 9/1974 | Ellison | 250/437 |
| 3,923,663 | 12/1975 | Reid | 210/251 |
| 4,101,777 | 7/1978 | Reid | 250/436 |

FOREIGN PATENT DOCUMENTS

| 845497 | 7/1952 | Fed. Rep. of Germany . | |
| 2400430 | 7/1975 | Fed. Rep. of Germany | 422/24 |
| 2513429 | 4/1976 | Fed. Rep. of Germany . | |
| 2622637 | 11/1977 | Fed. Rep. of Germany | 422/24 |
| 1359259 | 3/1964 | France . | |
| 2307575 | 11/1976 | France | 422/24 |

Primary Examiner—Benoît Castel
Attorney, Agent, or Firm—Karl W. Flocks

[57] ABSTRACT

The purification apparatus includes UV-tubes and secures a continuous and uniform disinfection or purification, respectively, of a flowing medium such as water, independent which portion of the space containing the UV-tubes is flowed through by such medium. The purification apparatus comprises a cylindrical pressure vessel with two chambers arranged on top of each other and separated from each other by a partition wall. The lower chamber comprises an inlet opening for the medium which is to be purified. The cylindrical upper chamber communicates with the lower chamber by inlet parts for the medium arranged on the partition wall and arranged groupwise along various concentric circles, each having a different radius. Inside of the vessel there is arranged an outlet tube, the upper portion of which is located in the upper chamber and comprises an inflow aperture at its upper end and the lower portion of which penetrates the partition wall and lower chamber and comprises at its lower end the discharge opening of the vessel. In each inlet part of the partition wall a UV-tube is supported at its lower end by the agency of guide vanes which produce a circulation of the incoming medium around the respective UV-tube. The UV-tubes extend through the upper chamber and penetrate an upper center plate and are supported at their upper end in a wall of the vessel remote from the inflow side.

6 Claims, 2 Drawing Figures

PURIFICATION APPARATUS

BACKGROUND OF THE INVENTION

1. Field of the Invention

The present invention relates to a purification apparatus having UV-tubes for purifying a flowing medium, such as water, which UV-tubes are arranged in an annular space of a vessel having inlet and outlet openings for such medium and which UV-tubes are arranged around a central tube and extend parallel thereto, which central tube penetrates the vessel and comprises at one end an outflow aperture and at the other end an inflow aperture for the medium and which is flowed through by the medium in a direction opposite to the direction of flow in the annular space.

2. Description of the Prior Art

The object of such purification apparatus is to disinfect, purify and degerminate, respectively, a flowing medium such as water without the need of adding any chemicals.

A known purification apparatus (prospect "Ultra-Violet Water Purifiers" of the Ultra Dynamics Corporation, Paterson, N. J.) comprises a cylindrical vessel through which UV-tubes (also called "burners") penetrate in the longitudinal direction thereof, which vessel is provided with an inflow opening arranged oppositely to an outflow opening arranged at axially oppositely arranged ends on relative to the circumference oppositely located sides of the vessel. Thereby the complete free inner space between the tubes is flowed through by the medium, which the closer it comes to the discharge opening the more it is purified or disinfected, respectively.

The German published patent application No. 1 003 404 discloses a purifier apparatus of the above described type. The medium which is to be purified is guided upwards over a central tube and bubbles via an inlet into an annular space in the vessel in which UV-radiators are arranged uniformly along a circular line extending coaxially to the central tube. However, this apparatus does not provide a uniform radiation in the annular space and the annular space is not uniformly flowed through by the liquid to be purified such that there is no guarantee that every part of the liquid mass or volume, respectively, receives the same quantity of energy for the destruction of the microorganisms.

The German published patent application No. 1 492 336 discloses a purifier means of a different design and comprising one centrally arranged UV-radiator only.

The U.S. Pat. No. 3,865,734 discloses a disinfection or purification, respectively, device which, however, does not utilize UV-rays, and is provided with several annular spaces, each having inlets and outlets.

SUMMARY OF THE INVENTION

Hence, it is a general object of the present invention to provide an improved purification, desinfection and degermination, respectively, apparatus, which secures that the complete annular space which is subjected to the rays of the UV-trubes receives a uniform or homogeneous, respectively, radiaition and which space is evenly flowed through by the medium subjected to the purification, such that every mass unit of the medium is subjected to an equal amount of radiation.

A further object of the invetnion is to provide a purification apparatus including UV-tubes which are distributed along a plurality of concentric circular lines, each having a different radius, which tubes are supported each by one of their ends in inlet ports for the medium in a wall of the vessel adjacent to the inlet opening thereof and supported by the other of their ends adjacent the inflow aperture in a wall of the vessel remote from the inlet thereof, whereby the outlet aperture of the tube acting as discharge tube for purified water forms the outlet opening of the vessel.

Another object is to support the UV-tubes by the agency of guide vanes which produce a circulatory flow of the inflowing medium around the respective UV-tubes. Thereby the relative location of the germs will be changed continuously with regard to the UV-tubes and accordingly a remaining of germs in the shadow of germs closer to the respective UV-tube and thus receiving an insufficient dose of radiation is successfully prevented.

A still further object of the invention is to provide a central discharge tube discharging the purified medium at a counter flow, thus allowing the arranging of inlet and outlet openings at one end only of the vessel. This is especially advantageous if the purification apparatus is mounted into a tube or pipe conduit. Accordingly an embodiment preferred for the practical application is one whereby its inlet opening and outlet opening have a common axis of the current flow of the medium to be purified whereby the UV-tubes as well as a straight-lined section of the central discharge tube located in the second chamber extend at an angle relative to mentioned axis of the current flow, whereby the straight-lined section of the central discharge tube passes via a pipe elbow inside the first chamber towards the discharge opening.

Yet further object of the present invention is to provide a means for a local controlling of the velocity of flow of the medium across the cross-section of the annular space adjacent to the inflow aperture of the discharge pipe. To this end and according to a preferred embodiment a center plate is mounted to the end of the discharge pipe bridging the cross-section of the annulus between the outer wall or jacket, respectively, of the vessel and the discharge pipe and which comprises parts which are aligned with the inlet ports in the wall of the vessel at the inlet opening side, whereby these ports through which the UV-tubes penetrate are groupwise arranged on a plurality of concentric circular lines, the center of which coincides with the center of the vessel or the central tube, respectively, and whereby the diameter of the ports in the center plate vary from circular line to circular line, whereby the diameter of the respective groups of ports decreases with increasing distance from the center of the vessel.

BRIEF DESCRIPTION OF THE DRAWINGS

The present invention will be more fully understood by reference to the following detailed description thereof, when read in conjunction with the amended drawings, wherein.

DETAILED DESCRIPTION OF THE PREFERRED EMBODIMENT

Figure 1:
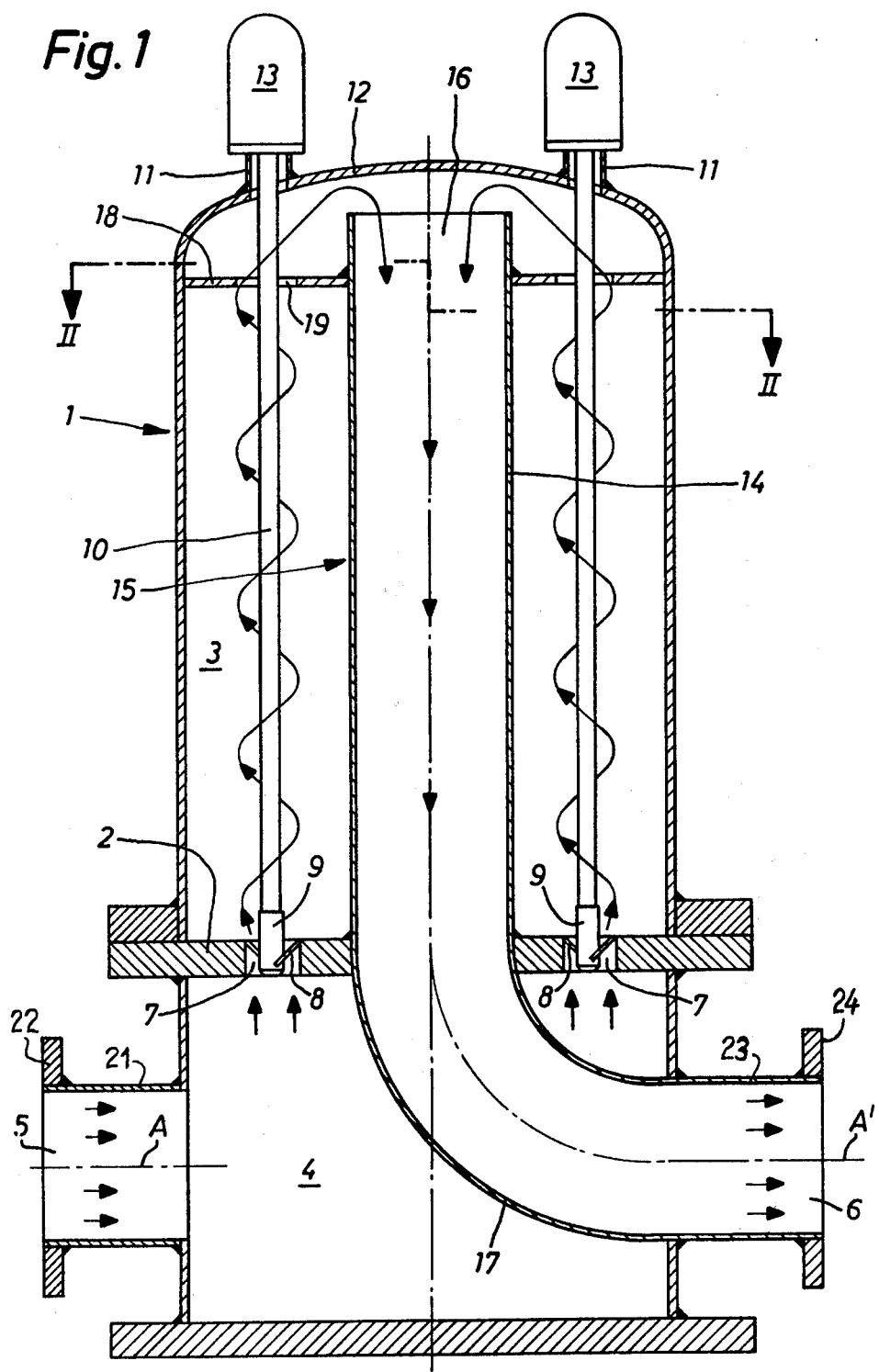
FIG. 1 is a view of a longitudinal section of a purifier means constructed in accordance with the present invention.

Describing now the drawings and considering initially the exemplary embodiment shown in FIG. 1 it will be understood that same comprises a cylindrical pressure vessel 1 comprising an upper chamber 3 and a lower chamber 4 arranged below chamber 3, which chambers 3, 4 are separated from each other by means of a partition wall 2. At one side of the lower chamber 4 there is provided an inlet opening 5 defined by a pipe stub 21 welded to the lower chamber 4, said pipe stub 21 having a flange 22 welded thereto. At the other, opposite side of chamber 4 there is provided a discharge opening 6 defined by a straight line pipe section 23 having a flange 24 welded thereto. The center line A of the pipe stub 21 representing the axis of flow of the medium entering the purifier apparatus is aligned with the axis of flow A' of the medium exiting the purifier which latter axis of flow A' is obviously defined by the center of the straight line pipe section 23. The cylindrical chamber 4 communicates via inlet ports 7 provided in the separating wall 2 with chamber 3. The exemplary embodiment comprises totally 18 such inlet ports 7.

Figure 2:
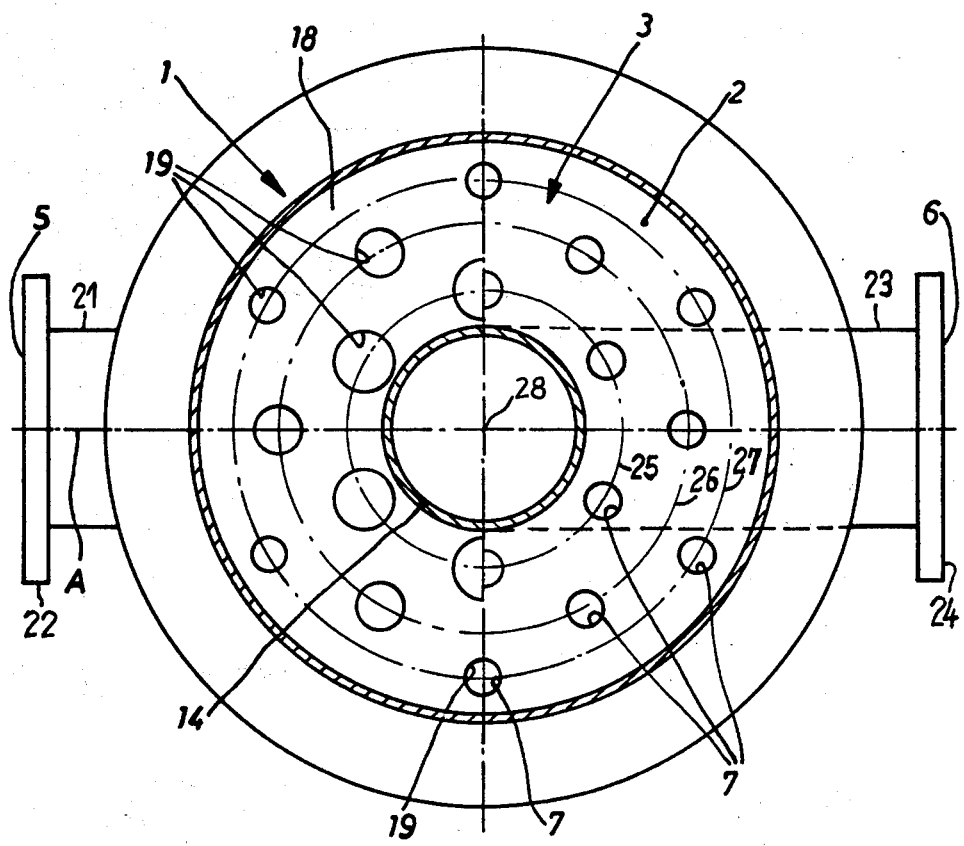
FIG. 2 is a section on a decreased scale along line II—II of FIG. 1, whereby a number of parts has been deleted for sake of clarity.

As shown in the right hand portion of FIG. 2 mentioned inlet ports 7 are arranged in three groups of six, each port 7 having the same diameter, whereby each group comprising ports 7 is distributed along a common circular line, each identified in FIG. 2 by the reference numerals 25, 26 and 27, respectively. The circular lines 25, 26 and 27 extend concentrically to each other and have together a common center 28 which also is the center of the cylindrical pressure vessel 1. Reference is made again to FIG. 1. The protective quartz tubes acting as protective jacket for the UV-tubes (not particularly shown in FIG. 2) arranged coaxially therein are identified by the reference numeral 10. Every such protective quartz tube 10 is supported by the agency of three guide vanes 8 via a guide 9 of the respective quartz tube 10 in one inlet port 7. The upper end of each protective quartz tube 10 penetrates an intermediate plate 18 which is accordingly provided with exit ports 19 and extends through pipe stubs 11 formed on top of the cover 12 of the vessel 1 and ends in a protective hood 13, through which hood the electrical connection to every UV-tube is made. Conclusively, the UV-tubes can be inserted into the vessel 1 from the outside and also removed from the vessel 1 from the outside.

The exit ports 19 of the annular intermediate plate 18 are aligned with the inlet ports 7. However, the diameter of each group describing one of mentioned concentric circular lines 25, 26, 27 varies with varying diameter of the circular lines 25, 26, 27. Specifically, the diameter of the inlet ports 7 decreases with increasing diameter of the circles 25, 26, 27. The reason therefore is the control of the mass flow per time unit at every opening 19, such that every portion of the mass of water flowing through the apparatus is subjected to the same does of radiation. Accordingly, the part of the flowing medium moving past the UV-tubes flowing in the area closer to the center of the vessel flows at a higher speed than such part of the medium flowing adjacent to the circumference of the vessel, such that the inner, more central portion of the medium, flowing in an area which is better illuminated, is subjected to the same UV-radiation as the portion adjacent the circumference.

In the center of chamber 3 there extends a vertical, straight line section 14 of a discharge pipe 15 having an inflow aperture 16 at its upper end.

The purification apparatus is quite suitable for the purification of a pressurized medium. It can e.g. be designed for an operating pressure of 16 bar.

A decisive advantage regarding the mounting of the inventive purification, disinfection or degermination, respectively, apparatus is the arrangement of inlet opening 5 and outlet opening 6. They have one common axis of flow A, A' and therefore, the apparatus can be mounted directly into a pressure pipe.

The annular space 3 defined by the partition wall 2 at the inlet ports and by the intermediate plate 18 contains no radiation impeding obstacles such as intermediate walls, guide vanes, etc. Which customarily have been arranged to influence the flowing medium. The desired flow, i.e. a controlling of the flowing medium is achieved here by the means defining the annular space, namely specifically the partition wall 2 and the intermediate plate 18 acting as distributing member for the medium to be purified as well as the specific arrangement of the UV-tubes relative to the separating wall 2 and to the intermediate plate 18.

The described apparatus ensures that independent from which area of the space flowed through the flowing medium actually flows, may this be the radially inner or radially outer section, a uniform degermination is achieved.

While there is shown and described a present preferred embodiment of the invention, it is to be distinctly understood that the invention is not limited thereto, but may be otherwise variously embodied and practiced within the scope of the following claims.

Accordingly,

What is claimed is:

1. In a purification apparatus comprising UV-tubes for the purification of a flowing medium such as water, which apparatus comprises a vessel provided with inlet and outlet openings for said medium and comprises further a centrally arranged tube, whereby said UV-tubes are arranged in an annular space of said vessel around said centrally arranged tube and extend parallel thereto, which centrally arranged tube extends through said vessel and is provided at one end with an outlet aperture and at the other end with an inflow aperture for said medium and is flowed through by said medium in a direction of flow prevailing in said annular space, an improvement comprising the distribution of said UV-tubes along a plurality of concentric circular lines extending in said annular space, whereby each circular line has a different radius, whereby each said UV-tubes is supported by one of its ends in inlet ports for said medium in a wall of said vessel adjacent said inlet opening and by the other of its ends located adjacent to said inflow aperture in a wall of said vessel arranged at a distance from said inlet opening, and whereby said outflow aperture of said tube acting as discharge tube for the purified medium forms said outlet opening of said vessel, said UV-tubes being supported by the agency of guide vanes in said inlet ports, which guide vanes generate a circulation of the inflowing medium around said respective UV-tubes, there being provided means for a local controlling of the flow speed of said medium across the cross-section of said annular space adjacent said inlet opening of said discharge tube, an intermediate plate being mounted to the end of said discharge tube and bridging the annular cross-section between the outer wall of said vessel and said discharge tube, which intermediate plate comprises through holes which are aligned with said inlet ports in said wall of said vessel adjacent said inlet opening, which said inlet ports and said through holes are penetrated by said UV-tubes and are, furthermore, groupwise arranged along coaxial circular lines having differing radiuses relative to the center of said vessel, and wherein each group of said through holes of said intermediate plate comprise a diameter differing from the other groups.

2. The purification apparatus of claim 1, wherein said inlet opening and said outlet opening are arranged in a first chamber and said UV-tubes are arranged in a second chamber and wherein said wall of said vessel located adjacent of said inlet opening forms a partition wall separating said two chambers from each other.

3. The purification apparatus of claim 2, wherein said inlet opening and said outlet opening comprise one common axis of flow of said medium and said UV-tubes as well as a straight line section of said discharge tube extend at an angle relative to said axis of flow and wherein said straight line section communicates by means of an elbow tube with said outlet opening, which elbow tube is arranged in said first chamber.

4. The purification apparatus of claim 3, wherein said UV-tubes and said straight line section of said discharge tube extend in a vertical direction and said axis of flow extends in a horizontal direction, and wherein said first chamber having said inlet and outlet openings is arranged below said second chamber which contains said UV-tubes.

5. The purification apparatus of claim 1, wherein said central discharge tube is made of a material forming a shield against UV-radiation.

6. The purification apparatus of claim 1 or claim 8, wherein said annular space comprises in the area between said wall of said vessel adjacent said inlet opening and said intermediate plate no obstruction to radiation such as intermediate walls, guide vanes and similar.

* * * * *